United States Patent
Nollenberger et al.

(10) Patent No.: US 9,844,511 B2
(45) Date of Patent: Dec. 19, 2017

(54) COATING COMPOSITION SUITABLE FOR PHARMACEUTICAL OR NUTRACEUTICAL DOSAGE FORMS

(75) Inventors: Kathrin Nollenberger, Frankfurt (DE); Jan Hendrik Schattka, Darmstadt (DE); Rene Leubert, Darmstadt (DE); Florian Hermes, Frankfurt (DE); Manfred Assmus, Bickenbach (DE); Christian Meier, Darmstadt (DE); Thomas Dassinger, Babenhausen (DE); Thomas Riermeier, Ober-Ramstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 4 days.

(21) Appl. No.: 14/118,078

(22) PCT Filed: Jun. 17, 2011

(86) PCT No.: PCT/EP2011/060094
§ 371 (c)(1),
(2), (4) Date: Nov. 15, 2013

(87) PCT Pub. No.: WO2012/171575
PCT Pub. Date: Dec. 20, 2012

(65) Prior Publication Data
US 2014/0086997 A1    Mar. 27, 2014

(51) Int. Cl.
| | |
|---|---|
| A61K 9/28 | (2006.01) |
| C08F 2/22 | (2006.01) |
| C08F 265/06 | (2006.01) |
| A61K 9/50 | (2006.01) |
| A61K 47/32 | (2006.01) |

(52) U.S. Cl.
CPC .......... *A61K 9/2886* (2013.01); *A61K 9/5026* (2013.01); *C08F 2/22* (2013.01); *C08F 265/06* (2013.01); *A61K 47/32* (2013.01)

(58) Field of Classification Search
CPC ... A61K 9/10; A61K 9/14; A61K 9/28; A61K 9/2816; A61K 9/2813; A61K 9/48; A61K 9/4816
USPC .......... 424/464, 465, 468, 473–482
See application file for complete search history.

(56) References Cited

U.S. PATENT DOCUMENTS

| | | | |
|---|---|---|---|
| 4,325,856 A | | 4/1982 | Ishikawa et al. |
| 4,330,338 A | * | 5/1982 | Banker .................. A23G 3/343 106/162.71 |
| 4,677,003 A | | 6/1987 | Redlich et al. |
| 5,643,602 A | * | 7/1997 | Ulmius .......... 424/462 |
| 2002/0155156 A1 | * | 10/2002 | Mulye .......... 424/482 |
| 2005/0090619 A1 | | 4/2005 | Yoshimura et al. |
| 2005/0137372 A1 | * | 6/2005 | Kulkarni et al. .......... 526/319 |
| 2006/0235131 A1 | | 10/2006 | Hughes et al. |
| 2006/0280798 A1 | | 12/2006 | Ensoli |
| 2010/0221324 A1 | | 9/2010 | Petereit et al. |
| 2010/0226978 A1 | | 9/2010 | Petereit et al. |

FOREIGN PATENT DOCUMENTS

| | | | | |
|---|---|---|---|---|
| DE | WO 2010105673 A1 | * | 9/2010 | .......... A61K 9/5078 |
| DE | WO 2011012163 A1 | * | 2/2011 | .......... A61K 9/282 |
| EP | 0 031 964 | | 7/1981 | |
| EP | 0 031 964 B1 | | 7/1981 | |
| EP | 0031964 B1 | * | 3/1986 | .......... C08F 263/02 |
| EP | 1 479 699 | | 11/2004 | |
| KR | 10-2011-0058835 A | | 6/2011 | |
| KR | 10-2011-0058836 A | | 6/2011 | |
| WO | 2009 036811 | | 3/2009 | |
| WO | WO 2010/034342 A1 | | 4/2010 | |
| WO | WO 2010/034344 A1 | | 4/2010 | |
| WO | WO 2011012163 A1 | * | 2/2011 | |

OTHER PUBLICATIONS

U.S. Appl. No. 14/115,632, filed Nov. 5, 2013, Schattka, et al.
U.S. Appl. No. 14/114,752, filed Oct. 30, 2013, Schattka, et al.
International Search Report dated Mar. 27, 2012 in PCT/EP11/060094 filed Jun. 17, 2011.
Garrett, et al., "Water-Borne Pressure-Sensitive Adhesives: Effects of Acrylic Acid and Particle Structure", Macromol. Symp. vol. 151, Feb. 2000, pp. 487-496, XP-000928071.
Written Opinion of the International Searching Authority dated Mar. 27, 2012 in PCT/EP11/060094 filed Jun. 17, 2011.
Office Action dated Jun. 29, 2015, in Russian Patent Application No. 2014101227 w/English translation.
Office Action dated Nov. 25, 2015, in Russian Patent Application No. 2014101227 w/English translation.
I.V. Pokrovskiy, Encyclopaedic Dictionary of Medical Terms, $2^{nd}$ edition. 2001, p. 531 w/English translation.
I.V. Pokrovskiy, Encyclopaedic Dictionary of Medical Terms, $2^{nd}$ edition, 2001, p. 603 w/English translation.
New GPC-IR Analysis of Polymeric Exdipients in Pharmaceutical Formulations, Jul. 2009, p. 1 "Summary".
Office Action dated Nov. 26, 2014, in Chinese Patent Application No. 201180071693.8 filed Jun. 17, 2011 w/English translation.

\* cited by examiner

*Primary Examiner* — Micah Paul Young
(74) *Attorney, Agent, or Firm* — Oblon, McClelland, Maier & Neustadt, L.L.P.

(57) ABSTRACT

The invention relates to a coating composition suitable for the coating of a pharmaceutical or nutraceutical dosage form, comprising a core comprising one or more pharmaceutical or nutraceutical active ingredients, wherein the coating composition is comprising at least 20% by weight of an enteric core/shell polymer composition derived from an emulsion polymerization process, wherein either the core of the core/shell polymer composition is formed by a water-insoluble, not cross-linked polymer or copolymer and the shell of the core/shell polymer composition is formed by an anionic polymer or copolymer or vice versa.

24 Claims, No Drawings

COATING COMPOSITION SUITABLE FOR PHARMACEUTICAL OR NUTRACEUTICAL DOSAGE FORMS

FIELD OF THE INVENTION

The present invention is concerned with a coating composition suitable for the coating of a pharmaceutical or nutraceutical dosage form, wherein the coating composition is comprising at least 20% by weight of an enteric core/shell polymer composition derived from an emulsion polymerisation process, wherein either the core is formed by a water-insoluble, not cross-linked polymer or copolymer and the shell is formed an anionic polymer or copolymer or vice versa.

TECHNICAL BACKGROUND (Meth)acrylate copolymers containing anionic groups are for instance disclosed in EP0704208B1, EP0704207A2, WO03/072087A1, WO2004/096185A1.

Controlled release pharmaceutical compositions with resistance against the influence of ethanol employing a coating comprising neutral vinyl polymers and excipients are known from WO2010/105672A1.

Controlled release pharmaceutical compositions with resistance against the influence of ethanol employing a coating comprising a polymer mixture and excipients are known from WO2010/105673A1.

PH-dependent controlled release pharmaceutical composition for narcotic drugs (opioids) with decreased susceptibility to the influence of ethanol on the release of active compound are known from WO2009/036812A1 and WO2010034342A1.

PH-dependent controlled release pharmaceutical compositions for drugs that are not opioids with decreased susceptibility to the influence of ethanol on the release of active compound are known from WO2009/036811A1 and WO2010034344A1.

WO2008/049657 describes the use of gastric resistant (meth)acrylate copolymers in retarded oral dosage forms as matrix formers for the active ingredient included in order to minimize the effect of acceleration or deceleration of the active ingredient release by the influence of ethanol under in-vitro conditions.

General Definitions

Singular forms like "a", "an", "the" or "another" as used in the description or in the claims shall be understood as to include the plural of the defined subject within the given definition or limits as well if not stated explicitly otherwise.

For instance the term "an enteric core/shell polymer composition" shall include one or more of theses compositions or copolymers e.g. mixtures thereof.

For instance the singular term "a (meth)acrylate copolymer" or "the (meth)acrylate copolymer" shall have the meaning of one or more (meth)acrylate copolymers within the given definition or limits of the monomer composition. Thus mixtures of different (meth)acrylate copolymers within the given definition or limits of the monomer composition are included in the sense of the invention. Singular terms like "a C4- to C18-alkyl ester of acrylic or methacrylic acid" or "another vinylic monomer" shall be understood in the same way to include one or more of these monomers.

Preferably the monomer ratios for copolymers disclosed herein add up to 100% by weight.

Problem and Solution

Pharmaceutical or nutraceutical compositions are designed to release the active ingredient in a manner of reproducible release curves. This shall result in desirable and reliable blood level profiles which shall provide an optimal therapeutic effect. If the blood level concentrations are too low, the active ingredient will not cause a sufficient therapeutic effect. If the blood level concentrations are too high, this may cause toxic effects. In both cases non optimal blood level concentrations of an active ingredient can be dangerous for the patient and shall therefore be avoided. A problem exists in that the ideal ratios assumed for the release of active ingredient during the design of a pharmaceutical or nutraceutical composition can be altered by the general living habits, thoughtlessness or by addictive behaviour of the patients with respect to the use of ethanol or ethanol-containing drinks. In these cases, the pharmaceutical or nutraceutical form which is actually designed for an exclusively aqueous medium is additionally exposed to an ethanol containing medium of greater or lesser strength. Since health authorities like for instance the US Food and Drug Administration (FDA) focus more and more on the ethanol problem, ethanol resistance may be an important registration requirement in the near future.

Since not all patients are aware of the risk of simultaneous taking of a controlled release pharmaceutical or nutraceutical form and ethanol-containing drinks or do not follow or are not able to follow appropriate warnings, advice or recommendations, there is a demand for controlled release pharmaceutical or nutraceutical compositions, especially for gastric resistant pharmaceutical or nutraceutical compositions, such that their mode of action is affected as little as possible by the presence of ethanol.

Conventional gastric resistant pharmaceutical or nutraceutical compositions if coated or uncoated are usually not resistant to alcohol at all. Therefore one problem of the present invention was to provide gastric resistant pharmaceutical or nutraceutical compositions which are resistant against the influence of ethanol.

Especially there is a problem for gastric resistant or enteric formulated compositions. These kinds of formulations are usually coated with a gastric resistant coating layer (enteric coating layer) onto the core which has the function that the release of the pharmaceutical or nutraceutical active ingredient in the stomach, respectively at pH 1.2 for 2 hours according to USP, shall not exceed 10, 8 or maybe 5%. This function ensures that acid-sensitive pharmaceutical or nutraceutical active ingredients are protected against inactivation and that pharmaceutical or nutraceutical active ingredients which may be irritate the stomach mucosa are not set free in too high amounts. On the other hand in many cases the release of the pharmaceutical or nutraceutical active ingredient in the intestine, respectively at pH 6.8 for one hour or less according to the USP method, is designed to exceed at least 50, 60, 80% or more. The presence of ethanol in concentrations of 20, 30 or 40% (volume/volume) in the gastric fluid usually leads to an increase to the release rates in the stomach. Due to distribution effect the effect of ingested ethanol is in the intestine not of that importance as in the stomach. Thus an effective protection against the influence of ethanol should prevent such an undesired increase of pharmaceutical or nutraceutical active ingredient in the stomach in the first place. Furthermore it may be desired that protection against the influence of ethanol shall at least not influence the comparably fast release rates at pH 6.8 in media without ethanol.

The several problems as discussed herein are solved by a coating composition suitable for the coating of a pharmaceutical or nutraceutical dosage form, comprising a core comprising one or more pharmaceutical or nutraceutical active ingredients, wherein the coating composition is comprising at least 20% by weight of an enteric core/shell polymer composition derived from an emulsion polymerisation process, wherein either the core of the core/shell polymer composition is formed by a water-insoluble, not cross-linked polymer or copolymer and the shell of the core/shell polymer composition is formed by an anionic polymer or copolymer or vice versa: that is the core of the core/shell polymer composition is formed by an anionic polymer or copolymer and the shell of the core/shell polymer composition is formed by a water-insoluble, not cross-linked polymer or copolymer.

DETAILED DESCRIPTION OF THE INVENTION

The invention is concerned with a coating composition suitable for the coating of a pharmaceutical or nutraceutical dosage form, comprising a core comprising one or more pharmaceutical or nutraceutical active ingredients, wherein the coating composition is comprising at least 20, at least 30, at least 40, at least 50, at least 60, at least 70, at least 80, at least 90 or 100% % by weight of an enteric core/shell polymer composition derived from an emulsion polymerisation process, wherein either the core of the core/shell polymer composition is formed by a water-insoluble, not cross-linked polymer or copolymer and the shell of the core/shell polymer composition is formed by an anionic polymer or copolymer or vice versa.

Food Grade or Pharmaceutical Grade Requirements

Suitable for the coating of a pharmaceutical or nutraceutical dosage form shall mean that the coating or binding composition shall fulfil all general and specific food grade or pharmaceutical grade requirements, including regulatory and legal requirements, for pharmaceutical or nutraceutical dosage forms. Of course all further excipients used in the pharmaceutical or nutraceutical dosage forms described herein shall also fulfil all general and specific food grade or pharmaceutical grade requirements, including regulatory and legal requirements, for pharmaceutical or nutraceutical dosage forms as well.

Coating Composition

The invention is concerned with a coating composition suitable for the coating of a pharmaceutical or nutraceutical dosage form, wherein the coating or binding composition is comprising at least 20, at least 30, at least 40, at least 50, at least 60, at least 70, at least 80, at least 90 or 100% by weight of an enteric core/shell polymer composition derived from an emulsion polymerisation process, wherein the either the core is formed by a water-insoluble, not cross-linked polymer or copolymer and the shell is formed an anionic polymer or copolymer or vice versa.

Aqueous Dispersion

The enteric core/shell polymer composition may be present in the coating composition in form of the solid phase of an aqueous dispersion with a solid content from 1 to 60% by weight. This means that the aqueous polymer dispersion, that is used to prepare the coating formulation, may contain 1 to 70% by weight of the coating composition as solid phase and 30 to 99% by weight as aqueous phase.

Powder or a Granulate

The enteric core/shell polymer composition may be present in the coating composition in the form of a dry powder or a granulate. In comparison to dispersion powders or a granulates have the advantage of less weight and less volume and can be stored in the dry stage for a long time without the risk of coagulation or of microbial contamination.

The solid from such an aqueous dispersion may be isolated by a spray drying process, freeze drying process or a coagulation process to give dry powder or a granulates. The powders or granulates may be converted into an aqueous dispersion again by redispersion in water.

Emulsion Polymerisation Process

In a typical emulsion polymerisation process first a core in the form of core particles is formed by polymerisation of the monomers for polymer or the copolymer of the core. Subsequently the monomers for polymer or the copolymer of the shell are polymerized in the same reaction mixture to give a shell around on the surface of the core particles.

It may as well possible to start the emulsion polymerisation process first by the addition of readily polymerized polymer particles such as cellulose particles or starch particles to the polymerisation mixture. Subsequently the monomers for polymer or the copolymer of the shell are polymerized in this reaction mixture to give a shell around on the surface of readily polymerized polymer core particles.

In the emulsion polymerization process, the operation may advantageously be carried out by the monomer emulsion feed process or the monomer feed process, respectively. For this, water is heated to the reaction temperature in the polymerization reactor. Surfactants and/or initiators may be added at this stage. Then—depending on the mode of operation—the monomer, a monomer mixture or an emulsion of either are fed to the reactor. This dosed liquid may contain initiators and/or surfactants or the initiator and/or the surfactant may be dosed parallel.

Alternatively, all monomers for the core can be charged into the reactor, before adding the initiator. This method is often referred to as batch process.

A chain transfer agent may be added to improve the process stability and reproducibility of the molecular weight ($M_w$). A usual chain transfer agent amount may be 0.05 to 1% by weight. A typical chain transfer agent may be for example thioglycolic acid 2-ethyl hexyl ester (TGEH) or n-dodecyl mercaptane (nDDM). However the chain transfer agent may be omitted in many cases, without affecting the properties according to the invention.

It is also possible to do a combination of both processes, by polymerizing a part of the monomers in the manner of a batch process, and feeding the other part afterwards. As known to the expert in the field, the type of process and mode of operation can be chosen, to achieve the desired particle size, sufficient dispersion stability, a stable production process and so on.

The average particle size of the polymer particles produced in the emulsion polymerization may range from 10 to 1000, 20 to 500 or 50 to 250 nm. The average particle size of the polymer particles may be determined by methods well known to a skilled person, for instance by the method of laser diffraction. The particle size may be determined by laser diffraction, using a Mastersizer® 2000 (Malvern). The values can be indicated as particle radius rMS [nm], which is half of the median of the volume based particle size distribution d(v,50).

Emulsifiers which may be used are especially anionic and non-ionic surfactants. The amount of emulsifier used is generally not more than 5% by weight, based on the polymer. Typical surfactants are for example alkyl sulfates (e.g. sodium dodecyl sulfate), alkyl ether sulfates, dioctyl sodium sulfosuccinate, polysorbates (e.g. polyoxyethylene (20) sorbitan monooleate), nonylphenol ethoxylates (nonoxynol-9) and others.

Beside those initiators conventionally used in emulsion polymerization (e.g. per-compounds, such as ammonium peroxodisulfate (APS), redox systems, such as sodium disulphite-APS-iron can be applied. Also water soluble azo-initiators may be applied and/or a mixture of initiators can be used. The amount of initiator is usually between 0.005 to 0.5% by weight, based on the monomer weight.

The polymerization temperature depends on the initiators within certain limits. For example, if APS is used it is advantageous to operate in the range from 60 to 90° C.; if redox systems are used it is also possible to polymerize at lower temperatures, for example at 30° C.

Enteric Core/Shell Polymer Composition

The core/shell polymer composition of the present invention has enteric properties. This mean the core/shell polymer composition is gastric resistant with no dissolution but swelling at acidic pH values, for instance at pH 1 to 4, but dissolves more or less rapidly at higher pH values, for instance from pH 5.0 on or higher. By being enteric the core/shell polymer composition confers gastric resistance and rapid active ingredient release in the intestine to the pharmaceutical or nutraceutical dosage form to or at which it is applied as a coating or as a binding agent. As a further advantage the core/shell polymer composition also confers gastric resistance in the presence of ethanol in the stomach.

A core/shell polymer composition is derived from an emulsion polymerisation process in at least two steps. In the first process step core polymer particles are formed by monomer polymerisation in the emulsion. In the second step the shell is polymerized onto these core particles by subsequent monomer polymerisation in the same emulsion.

In rare cases, as known to the expert in the art, the second polymer is not deposited on the surface of the initially formed particles, but enters into the centre of the particle instead. As a result, the firstly prepared polymer is squeezed to the border of the particle to form the shell. Thus an inversed structure, with the firstly prepared polymer as shell polymer, and the subsequently prepared polymer as a core polymer, results. This happens only in special cases; usually than the secondly prepared polymer is much more hydrophobic than the firstly prepared polymer.

Between the two extremes of a regular and an inversed core/shell structure, many other structures are possible, and have been observed; in the literature one is for example called partially engulfed.

While such structural variations may indeed have influence on the properties of the polymer composition, it is not always possible to determine exactly which structure was formed. In this invention therefore the firstly prepared polymer will be called the core polymer, even if that may not describe the resulting structure correctly in all cases.

In most cases by far, the regular core/shell structure will form.

The invention relates to a core/shell polymer composition suitable as a coating or binding agent in a pharmaceutical or nutraceutical dosage form, where the core/shell polymer composition is derived from an emulsion polymerisation process, wherein the either the core is formed by a water-insoluble polymer or copolymer and the shell is formed an anionic polymer or copolymer or vice versa.

The invention discloses explicitly each possible combination of any water-insoluble polymer or copolymer described in here as a core with any anionic polymer or copolymer described in here as the shell, as well as each possible combination of any anionic polymer or copolymer described in here as core with any water-insoluble polymer or copolymer described in here as a shell.

The core may be formed by a water-insoluble polymer or copolymer and the shell may be formed by an anionic polymer or copolymer or vice versa.

Most Preferred the core is formed by a water-insoluble polymer or copolymer and the shell is formed an anionic polymer or copolymer.

In some cases the shell may be formed by a water-insoluble polymer or copolymer and the core is formed an anionic polymer or copolymer. In some cases this may be the result of an inversion of the phases during the emulsion polymerization process.

The polymer or copolymer of the core is preferably water-insoluble polymer and not cross-linked. Not cross-linked means that the water-insoluble polymer or copolymer is not polymerized from monomers containing reactive side groups which are capable to cross-link the linear polymer chains. Such reactive side groups which are capable to cross-link the linear polymer chains may be a vinylic side group or an allylic side group. For example monomers with more than one vinylic group or with one vinylic and one or more allylic groups are avoided. For instance monomers like ethyleneglycol-di-methacrylate (EGDMA) are not contained.

In many cases for polymers that are not cross-linked, a solvent can be found, in which the polymer can be dissolved.

Core/Shell Ratios

The weight of the core may be 10 to 95% of the weight of the total core/shell polymer composition.

The core/shell polymer composition may comprise, comprise essentially or consist of 10 to 95, or 20 to 90, preferably 30 to 80% by weight of the polymers or copolymers of the core. The core/shell polymer composition may comprise, comprise essentially or consist of 5 to 90, or 10 to 80, preferably 20 to 70% by weight of the polymers or copolymers of the shell. Core and shell may add up to 100%. Usually there is one core and one shell in the core/shell polymer composition. However it is also possible that more than one shell, i.e. two or more different shell polymers or copolymers may be applied to one core polymers or copolymers.

It has been surprisingly found that standard, non-core/shell enteric polymer coatings can be substituted by coatings of the same thickness, based on the core/shell polymer compositions as disclosed without impairing the enteric properties. Furthermore the resistance against ethanol is improved. At the same time the total amount of anionic groups in the coating is reduced. This is of further advantage because the maximum daily intake for which the amount of anionic groups is usually limiting can be increased.

Different Micro Structural and Physical Behaviour

Due to their mode of preparation the core/shell polymer composition according to the present invention show a different micro structural and also a different physical behaviour compared to simple mixtures of the same two polymers or copolymers at the same weight ratios. As each polymer particle of the core/shell dispersion contains both core and shell polymer, the two polymers are evenly distributed. In contrast, for a physical mixture of two polymer dispersions, particles of one and the other polymer are distributed randomly; adjacent particles of the same polymer are forming larger domains.

The difference in the microstructure may in certain cases be visualized under a light microscope where the core/shell polymer compositions may show a more homogeneous structure without visible phase separation. The difference in the physical behaviour may show in a more or less unique intermediate glass transition temperature compared to two glass transition temperature peaks in the simple mixtures. Thus core/shell polymer compositions of the present invention result in more homogenous mixtures of the two polymers than it can be achieved with pure physically mixtures or simple mixtures. This apparently results in more homogenous coatings with an assumed finer microstructure. Fewer incompatibilities between the two polymers occur. Coated pharmaceutical or nutraceutical drug forms become more reliable in their active ingredient release behaviour and more stable under storage conditions. Positive effects on the tensile strength and differences in the film forming temperatures may be also observed.

In some cases the release behaviour of the coating compositions employing the core/shell polymer compositions as described herein differ from that of the corresponding none inventive enteric coatings. For instance in some cases it was observed that when the EUDRAGIT® FS type polymer is used in a certain core/shell polymer compositions the release the active ingredient starts already at pH 6.8 and is faster while the start of the release with the corresponding polymer mixture is around pH 7.0 and slower. Thus the inventive coating compositions employing the core/shell polymer compositions as described herein may also be used to modify the release behaviour of certain polymer combinations. This is of additional advantage since it broadens the freedom of the skilled person in the release design of pharmaceutical or nutraceutical dosage forms.

Preferred Core Polymer or Copolymer
Water-Insoluble, not Cross-Linked Polymers or Copolymers Water-insoluble, not cross-linked polymers or copolymers which may be preferably used as the core of the core/shell composition may be selected from the group of (meth)acrylate polymers or copolymers or from the group of polyvinyl polymers or copolymers or from the group of celluloses.

Water-insoluble, not cross-linked polymers or copolymers in the sense of the invention are polymers which do not dissolve in water or are only swellable in water over of the whole range of pH 1-14. Water-insoluble polymers may be at the same time polymers containing not more than 12% of monomer residues with ionic side groups, like for instance EUDRAGIT® NE/NM or EUDRAGIT® RL/RS polymers.

The water-insoluble polymers may contain less than 10, less than 5, less than 2, less than 1% by weight or any monomer residues with ionic side groups, preferably not more than 12, not more than 6% by weight or any monomer residues with cationic side groups.

The one or more water-insoluble polymers or one or more cellulosic polymers may preferably contain less than 5% by weight, preferably not more than 2% by weight, more preferably not more than 1 or 0.05 to 1% by weight, of monomer residues with anionic side groups.

Other kinds of water-insoluble, not cross-linked polymers in the sense of the invention may be vinyl copolymers like polyvinylacetate, including derivates of polyvinylacetate. The polyvinylacetate may be present in the form of a dispersion. One example is the type Kollicoat® SR 30 D (BASF), polyvinylacetate dispersion, stabilized with povidone and Na-laurylsulfate.

A suitable water-insoluble, not cross-linked cellulose may be for instance methyl cellulose or ethyl cellulose.

The water-insoluble polymers, not cross-linked may preferably belong to the group of (meth)acrylate copolymers.
EUDRAGIT® NE 30D/EUDRAGIT® NM 30D-Type Polymers A water-insoluble copolymer which may be preferably used as the core of the core/shell composition may be a copolymer composed of free-radical polymerized units of more than 95% by weight, in particular to an extent of at least 98% by weight, preferably to an extent of at least 99% by weight, in particular to an extent of at least 99% by weight, more preferably to an extent of 100% by weight, of (meth)acrylate monomers with neutral moieties especially $C_1$- to $C_4$-alkyl moieties. These kinds of polymers do not dissolve in water or are only swellable in water over of the whole range of pH 1-14.

Suitable (meth)acrylate monomers with neutral moieties are, for example, methyl methacrylate, ethyl methacrylate, butyl methacrylate, methyl acrylate, ethyl acrylate, butyl acrylate. Preference is given to methyl methacrylate, ethyl acrylate and methyl acrylate.

Methacrylate monomers with anionic functional groups, for example acrylic acid and/or methacrylic acid, may be present in small amounts of less than 5% by weight, preferably not more than 2% by weight, more preferably not more than 1 or 0.05 to 1% by weight.

Suitable examples are neutral or virtually neutral (meth) acrylate copolymers composed of 20 to 40% by weight of ethyl acrylate, 60 to 80% by weight of methyl methacrylate and 0 to less than 5% by weight, preferably 0 to 2 or 0.05 to 1% by weight of methacrylic acid or any methacrylic acid (EUDRAGIT® NE 30D or EUDRAGIT® NM 30D type).

EUDRAGIT® NE 30D and Eudragit® NM 30D are dispersions containing 30% by weight of copolymers composed of free-radically polymerized units of 30% by weight of ethyl acrylate and 70% by weight of methyl methacrylate.

Preference is given to neutral or essentially neutral methyl acrylate copolymers which, according to WO 01/68767, have been prepared as dispersions using 1-10% by weight of a nonionic emulsifier having an HLB value of 15.2 to 17.3. The latter offer the advantage that there is no phase separation with formation of crystal structures by the emulsifier (Eudragit® NM 30D type).

According to EP 1 571 164 A2, corresponding, virtually neutral (meth)acrylate copolymers with small proportions of 0.05 to 1% by weight of monoolefinically unsaturated C3-C8-carboxylic acids can, however, also be prepared by emulsion polymerization in the presence of comparatively small amounts of anionic emulsifiers, for example 0.001 to 1% by weight.

EUDRAGIT® RL/RS-Type Polymers

A further water-insoluble copolymer which may be preferably used as the core of the core/shell composition may be a copolymer composed of free-radical polymerized units of 85 to 98% by weight of free-radical polymerized $C_1$ to $C_4$ alkyl esters of acrylic or methacrylic acid and 15 to 2% by weight of (meth)acrylate monomers with a quaternary amino group in the alkyl moiety. These kinds of polymers do not dissolve in water or are only swellable in water over of the whole range of pH 1-14.

Alkyl(Meth)Acrylate Copolymers

Water-insoluble copolymers which may be used as the core of the core/shell composition may be alkyl(meth)

acrylate copolymers without any functional groups in the alkohol part of the ester monomers. The polymer may for example be polymerized out of 100% by weight of n-butyl methacrylate (n-BMA).

Preferred Shell Polymer or Copolymer

Anionic Polymer or Copolymers

The anionic polymer or copolymer which may be preferably used as the shell of the core/shell composition may be selected from the group of (meth)acrylate polymers or copolymers or polyvinyl polymers or copolymers or celluloses. The anionic polymer or copolymers are preferably not cross-linked.

Anionic Celluloses

Suitable anionic polymer or copolymers may be carboxymethyl cellulose and its salts (CMC, Na-CMC, Blanose®, Tylopur®), carboxymethylethyl cellulose and its salts, cellulose acetate phthalate (CAP), cellulose acetate succinate (CAS), cellulose acetate trimelliate (CAT), hydroxypropyl methyl cellulose phthalate (HPMCP, HP50, HP55) or hydroxypropylmethyl cellulose acetate succinate (HPMCAS-LF, -MF, -HF).

Anionic Polyvinyl Polymers

Suitable polyvinyl polymers or copolymers may comprise structural units that are derived from unsaturated carboxylic acids other than acrylic acid or methacrylic acid as exemplified by polyvinylacetatephthalate or a copolymer of vinylacetate and crotonic acid 9:1.

Anionic (Meth)Acrylate Copolymers

Anionic (meth)acrylate copolymers may comprise 25 to 95, preferably 40 to 95, in particular 60 to 40, % by weight free-radical polymerized $C_1$- to $C_{18}$-alkyl esters, preferably $C_1$- to $C_8$- or $C_1$- to $C_4$-alkyl esters alkyl esters of acrylic or of methacrylic acid and 75 to 5, preferably 60 to 5, in particular 40 to 60, % by weight (meth)acrylate monomers having an anionic group.

The proportions mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as, for example, hydroxyethyl methacrylate or hydroxyethyl acrylate, to be present. It is preferred that no further monomers capable of vinylic copolymerization are present.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate. A (meth)acrylate monomer having an anionic group is, for example, acrylic acid, with preference for methacrylic acid.

Examples for Suitable Anionic (Meth)Acrylate Copolymers

A suitable anionic (meth)acrylate copolymer may be comprising, essentially comprising, containing or consisting of polymerized units of
  10 to 40% by weight of acrylic or methacrylic acid
  10 to 80% by weight of a $C_4$- to $C_{18}$-alkyl ester of acrylic or methacrylic acid and optionally
  0 to 60% by weight of another vinylic monomers without cross-linking side chains.

$C_4$- to $C_{18}$-alkyl ester of acrylic or methacrylic acid are preferably chosen from n-butyl methacrylate, 2-ethylhexyl acrylate, 2-ethylhexyl methacrylate, isodecyl methacrylate and lauryl methacrylate.

Another vinylic monomer is a vinylic monomer which is not acrylic or methacrylic acid or a $C_4$- to $C_{18}$-alkyl ester of acrylic or methacrylic acid. Another vinylic monomer may be preferably a $C_1$- to $C_3$-alkyl ester of acrylic or methacrylic acid, which are methyl acrylate, ethyl acrylate, propyl acrylate, methyl methacrylate, ethyl methacrylate or propyl methacrylate. Another vinylic monomer may be hydroxyethyl methacrylate, hydroxypropyl methacrylate, poly(ethylenglycol)methylether acrylat, poly(ethylenglycol)methylether methacrylat, poly(propylenglycol)methylether acrylat, poly(propylenglycol)methylether methacrylat or styrene.

Preferably the anionic (meth)acrylate copolymer is comprising, essentially comprising or containing polymerized units of
  10 to 40% by weight of acrylic or methacrylic acid
  10 to 50% by weight of ethyl acrylate
  10 to 80% by weight of a $C_4$- to $C_{18}$-alkyl ester of acrylic or methacrylic acid and optionally
  0 to 20 by weight of methyl methacrylate.

Preferably the anionic (meth)acrylate copolymer is comprising, essentially comprising or containing polymerized units of
  20 to 40% by weight of methacrylic acid,
  20 to 40% by weight of n-butyl methacrylate and
  30 to 50% by weight of ethyl acrylate Preferably the anionic (meth)acrylate copolymer is comprising, essentially comprising or containing polymerized units of
  20 to 40% by weight of methacrylic acid,
  30 to 50% by weight of 2-ethylhexyl acrylate,
  15 to 40% by weight of ethyl acrylate and optionally
  0 to 20% by weight of methyl methacrylate.

Preferably the anionic (meth)acrylate copolymer is comprising, essentially comprising or containing polymerized units of
  10 to 40% by weight of methacrylic acid,
  20 to 70% by weight of 2-ethylhexyl methacrylate and
  10 to 50% by weight of ethyl acrylate.

Preferably the anionic (meth)acrylate copolymer is comprising, essentially comprising or containing polymerized units of
  20 to 40% by weight of methacrylic acid,
  20 to 50% by weight of 2-ethylhexyl methacrylate and
  20 to 50% by weight of ethyl acrylate.

Preferably the anionic (meth)acrylate copolymer is comprising, essentially comprising or containing polymerized units of
  10 to 35% by weight of methacrylic acid,
  40 to 70% by weight of 2-ethylhexyl methacrylate and
  10 to 30% by weight of ethyl acrylate.

Preferably the anionic (meth)acrylate copolymer is comprising, essentially comprising or containing polymerized units of
  20 to 40% by weight of methacrylic acid,
  20 to 40% by weight of isodecyl methacrylate and
  40 to 50% by weight of ethyl acrylate.

Preferably the anionic (meth)acrylate copolymer is comprising, essentially comprising or containing polymerized units of
  20 to 40% by weight of methacrylic acid,
  20 to 40% by weight of lauryl methacrylate and
  30 to 50% by weight of ethyl acrylate.

Further Characteristics of the Anionic (Meth)Acrylate Copolymers,

Further characteristics of the anionic (meth)acrylate copolymer, especially of the anionic (meth)acrylate copolymers described above may be summarized as follows.

Preferably the (meth)acrylate copolymer may be characterized by a mean glass transition temperature from 25 to 120 or 40 to 80° C. (determined by DSC according to DIN EN ISO 11357).

Preferably the (meth)acrylate copolymer may be characterized by a minimum film forming temperature of 50° C. or less (determined according to DIN ISO 2115).

Preferably the (meth)acrylate copolymer may be characterized by a mean molecular weight $M_w$ is 80.000 or more (determined by gel permeation chromatography, GPC).

Further Suitable Anionic (Meth)Acrylate Copolymer

Suitable anionic (meth)acrylate copolymers are those composed of 40 to 60% by weight methacrylic acid and 60 to 40% by weight methyl methacrylate or 60 to 40% by weight ethyl acrylate (EUDRAGIT® L or EUDRAGIT® L100-55 types).

EUDRAGIT® L is a copolymer of 50% by weight methyl methacrylate and 50% by weight methacrylic acid. The pH of the start of the specific active ingredient release in intestinal juice or simulated intestinal fluid can be stated to be pH 6.0.

EUDRAGIT® L 100-55 is a copolymer of 50% by weight ethyl acrylate and 50% by weight methacrylic acid. EUDRAGIT® L30 D-55 is a dispersion comprising 30% by weight EUDRAGIT® L 100-55. The pH of the start of the specific active ingredient release in intestinal juice or simulated intestinal fluid can be stated to be pH 5.5.

Likewise suitable are anionic (meth)acrylate copolymers composed of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally suitable is a copolymer composed of
20 to 34% by weight methacrylic acid and/or acrylic acid,
20 to 69% by weight methyl acrylate and
0 to 40% by weight ethyl acrylate and/or where appropriate
0 to 10% by weight further monomers without cross-linking side chains capable of vinylic copolymerization,
with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable is a copolymer composed of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate
0 to 10% by weight further monomers without cross-linking side chains capable of vinylic copolymerization,
where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of 20 to 33, preferably 25 to 32, particularly preferably 28 to 31% by weight methacrylic acid or acrylic acid, with preference for methacrylic acid, 5 to 30, preferably 10 to 28, particularly preferably 15 to 25% by weight methyl acrylate, 20 to 40, preferably 25 to 35, particularly preferably 18 to 22% by weight ethyl acrylate, and more than 10 to 30, preferably 15 to 25, particularly preferably 18 to 22% by weight butyl methacrylate, where the monomer composition is chosen so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The copolymer preferably consists essentially to exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinylmalonic acid, styrene, vinyl alcohol, vinyl acetate and/or derivatives thereof.

Preparation of Anionic (Meth)Acrylate Copolymers

The anionic (meth)acrylate copolymers may be prepared in a manner known per se by free-radical polymerization of the monomers (see, for example, EP 0 704 207 A2 and EP 0 704 208 A2) by radical polymerisation of the monomers in the presence of polymerisation initiators and optionally molecular weight regulators. The copolymers according to the invention are prepared by free-radical emulsion polymerization in aqueous phase in the presence of, preferably, anionic emulsifiers. The process of emulsion polymerization is well known in the art for instance as described in DE-C 2 135 073.

The average molecular weight Mw (weight average, determined for example by measuring the solution viscosity) of the anionic (meth)acrylate copolymers may be for example in the range from 80 000 to 1 000 000 (g/mol).

Process for Preparing an Anionic (Meth)Acrylate Copolymer

An anionic (meth)acrylate copolymer may be produced by radical polymerisation of the monomers in the presence of polymerisation initiators. Molecular weight regulators may be added. The preferred polymerisation method is emulsion polymerisation.

Suitable Core/Shell Combinations

Any possible combination of any polymer or copolymer type described herein as a possible core polymer with any polymer or copolymer type described herein as a possible shell polymer shall be explicitly disclosed herein. However certain combinations are preferred.

EUDRAGIT® L100-55 Type Copolymer as Core or Shell Polymer

The EUDRAGIT® L100-55 type copolymer is a copolymer polymerized out of 40-60, preferably 45-55, especially 50% by weight ethyl acrylate (EA) and 40-60, preferably 45-55, especially 50% by weight methacrylic acid (MAS). Preferred is EUDRAGIT® L 100-55 which is a copolymer of 50% by weight ethyl acrylate and 50% by weight methacrylic acid (EUDRAGIT® L30 D-55 is a dispersion comprising 30% by weight EUDRAGIT® L 100-55).

EUDRAGIT® L Type Copolymer as Core or Shell Polymer

The EUDRAGIT® L type copolymer is a copolymer polymerized out of 40-60, preferably 45-55, especially 50% by weight methyl methacrylate (MMA) and 40-60, preferably 45-55, especially 50% by weight methacrylic acid (MAS). Preferred is EUDRAGIT® L which is a copolymer of 50% by weight methyl methacrylate (MMA) and 50% by weight methacrylic acid (EUDRAGIT® L30D is a dispersion comprising 30% by weight EUDRAGIT® L).

EUDRAGIT® S Type Copolymer as Core or Shell Polymer

The EUDRAGIT® S type copolymer is a copolymer polymerized out of 60-80, preferably 65-75, especially 70% by weight methyl methacrylate (MMA) and 20-40, preferably 25-35, especially 30% by weight methacrylic acid (MAS). Preferred is EUDRAGIT® S100 which is a copolymer of 70% by weight methyl methacrylate (MMA) and 30% by weight methacrylic acid.

EUDRAGIT® NE/NM Type Copolymer as Core or Shell Polymer

The EUDRAGIT® NE/NM type copolymer is a Copolymer polymerized out of 20 to 40% by weight of ethyl acrylate, 60 to 80% by weight of methyl methacrylate and 0 to less than 5% by weight, preferably 0 to 2 or 0.05 to 1% by weight of methacrylic acid or any methacrylic acid (EUDRAGIT® NE 30D or EUDRAGIT® NM 30D type). Preferred are copolymers composed of free-radically polymerized units of 30% by weight of ethyl acrylate and 70% by weight of methyl methacrylate (EUDRAGIT® NE 30D and EUDRAGIT® NM 30D are dispersions containing 30% by weight of copolymers composed of free-radically polymerized units of 30% by weight of ethyl acrylate and 70% by weight of methyl methacrylate.)

EUDRAGIT® FS Type Copolymer as Core or Shell Polymer

The EUDRAGIT® FS type copolymer is a copolymer polymerized out of 10 to 30% by weight methyl methacrylate, 50 to 70% by weight methyl acrylate and 5 to 15% by weight methacrylic acid (EUDRAGIT® FS type). Preferred is EUDRAGIT® FS which is a copolymer of 25% by weight methyl methacrylate, 65% by weight methyl acrylate and 10% by weight methacrylic acid (EUDRAGIT® FS 30 D is a dispersion comprising 30% by weight EUDRAGIT® FS.).

Butylmethacrylate Homopolymer as Core Polymer

The n-butylmethacrylate homopolymer is a polymer polymerized out of 100% by weight n-butyl acrylate (n-BMA).

TABLE 1

Possible Core/Shell combinations

| Combination No. | Core | Shell | Possible weight ratios Core/Shell |
|---|---|---|---|
| 1 | EUDRAGIT ® L100-55 type | EUDRAGIT ® NE/NM type | 60/40 to 40/60 Preferred 50/50 |
| 2 | EUDRAGIT ® L100-55 type | EUDRAGIT ® NE/NM type | 90/10 to 70/30 Preferred 80/20 |
| 3 | EUDRAGIT ® NE/NM type | EUDRAGIT ® L100-55 type | 60/40 to 40/60 Preferred 50/50 |
| 4 | EUDRAGIT ® NE/NM type | EUDRAGIT ® L100-55 type | 90/10 to 70/30 Preferred 80/20 |
| 5 | EUDRAGIT ® FS type | EUDRAGIT ® NE/NM type | 60/40 to 40/60 Preferred 50/50 |
| 6 | EUDRAGIT ® FS type | EUDRAGIT ® NE/NM type | 90/10 to 70/30 Preferred 80/20 |
| 7 | EUDRAGIT ® NE/NM type | EUDRAGIT ® FS type | 60/40 to 40/60 Preferred 50/50 |
| 8 | EUDRAGIT ® NE/NM type | EUDRAGIT ® FS type | 90/10 to 70/30 Preferred 80/20 |
| 9 | Butylmethacrylate homopolymer | EUDRAGIT ® L100-55 type | 60/40 to 40/60 Preferred 50/50 |

Release of the Pharmaceutical or Nutraceutical Active Ingredient for the Coating Composition The release, according to USP, of the pharmaceutical or nutraceutical active ingredient is not more than 10, not more than 8 or not more than 5% under in-vitro conditions at pH 1.2 after 2 hours in 0.1 molar HCl with and without the addition of 20, 30 or 40% (v/v) ethanol.

The release according to USP of the pharmaceutical or nutraceutical active ingredient is at least 50, at least 60, at least 80% under in-vitro conditions at pH 6.8 after 45 or after 60 minutes in buffered medium (phosphate buffered saline, pH 6.8, European Pharmacopoeia 4003200).

Alternatively the release of the pharmaceutical or nutraceutical active ingredient may be at least 50, at least 60, at least 80% under in-vitro conditions at pH 7.2 after 45 or after 60 minutes in buffered medium according to USP for instance when copolymers of the EUDRAGIT® FS type are used as core or shell polymers. EUDRAGIT® FS type copolymers show a start of the specific active ingredient release in intestinal juice or simulated intestinal fluid around pH 7.0.

Thus the release of the pharmaceutical or nutraceutical active ingredient may be at least 50, at least 60, at least 80% under in-vitro conditions at pH 6.8 or at pH 7.2 after 45 or after 60 minutes in buffered medium according to USP.

The USP (USP=United States Pharmacopoeia) which may be preferably used is USP32/NF27 (NF=National Formulary), apparatus II, paddle method, 50 rpm for tablets or paddle or basket method 50 to 100 rpm, depending on the monograph, for pellets.

Core Comprising the Pharmaceutical or Nutraceutical Active Ingredient

The core comprises one or more pharmaceutical or nutraceutical active ingredients as the core or as a part of the core. The one or more pharmaceutical or nutraceutical active ingredients may be more or less homogeneously distributed in a matrix structure within the core structure or may form the core as a crystallized structure. The one or more pharmaceutical or nutraceutical active ingredients may alternatively be present as a part of the core in the form of a layer onto a carrier pellet. Thus the core is an unfinished, coated or uncoated, but still to be coated pharmaceutical or nutraceutical dosage form.

The core, respectively the pharmaceutical or nutraceutical dosage form to be coated by the coating composition may comprise or may contain a neutral carrier pellet, for instance a sugar sphere or non-pareilles, on top of which the active ingredient is bound in a binder, such as lactose or polyvinyl pyrrolidon.

The core may alternatively comprise a pellet in the form of a polymeric matrix in which the active ingredient is bound. The core may comprise an uncoated pellet consisting of a crystallized active ingredient. The core may also comprise its own coating for instance a sustained release coating. Such an already coated core may then be coated by the coating composition described herein.

The core may be uncoated or may comprise a coating, which is different from the coating derived from coating composition described herein. The core may be a coated pellet, for instance with a sustained release coating, an uncoated or coated tablet, an uncoated or coated mini tablet or an uncoated or coated capsule. The core may also comprise a so called "sub coat" as an outer layer.

The core comprises at least more than 80, more than 90, more than 95, more than 98, preferably 100% of the total amount of one or more pharmaceutical or nutraceutical active ingredients present in the gastric resistant pharmaceutical or nutraceutical dosage form.

In some cases it may be useful that the coating composition may comprise, additionally to the active ingredient present in the core, a partial amount, preferably less than 20, less than 10, less than 5 less than 2% by weight of the total amount of one or more pharmaceutical or nutraceutical active ingredients, for instance in order to provide an initial dose of the active ingredient. In this case the coating composition has the function as a binding agent or as a binder for the additional active ingredient. Preferably the coating composition comprises any active ingredient.

Coating

Coating suspensions may be applied by spray or powder coating processes following known processes. As a rule the coated compositions may be cured at elevated temperatures for example 24 hours at 40° C. or 60° C. after the spray coating in order to provide reproducible and stable functionality.

The polymer dry weight gain of the coating layer may be at least 2.5, at least 3.5, at least 4, preferably 4 to 30, preferably 4 to 20, more preferably 5 to 18, or most preferably 10 to 18 mg/cm$^2$ surface area. This may correlate to 2-60% polymer dry weight gain related to the weight of the core. In the case of coated tablets the polymer dry weight gain related to the weight of the core (tablet core: around 1-25 or 1-10 mm in diameter or length) may be 2-30%. In the case of coated pellets the polymer dry weight gain related to the weight of the core (pellet core: 0.1 to 1.5 mm in diameter) may be 10-60%.

Pellets are typically coated with at least 4 weight % of polymer, based on the weight of the uncoated pellets (i.e. 4% polymer weight gain). A better protection of the active ingredient is achieved with a thicker coating of 6%, 8% or 10% polymer weight gain.

Usually not more than 40% polymer weight gain of coating are applied to pellets, as then the time for the dissolution of the coating layer starts getting too long. In many cases less than 30%, less than 25%, or less than 20% polymer weight gain are sufficient.

On tablets and capsules, a coating with typically at least 2 mg polymer per cm$^2$ of surface is applied. In most cases at least 3 mg, 4 mg or 6 mg of polymer per cm$^2$ of surface are applied. Coating amounts of more than 40 mg of polymer per cm$^2$ of surface are hardly ever used; typically less than 30 mg, less than 25 mg or less than 20 mg of polymer per cm$^2$ of surface are applied. In general more coating thickness is required for capsules and oblong shaped tablets, while more spherical dosage forms require less coating.

Top Coat and Sub Coats

The gastric resistant pharmaceutical or nutraceutical dosage according to the invention may further comprise a so called "sub coat" or a so called "top coat" or both. The expressions sub coat and top coat are well known to the person skilled in the art.

A sub coat may be located between the core and the gastric resistant (enteric) coating layer. A sub coat may have the function to separate substances of the core from substances of the controlling layer which may be incompatible with each other. The sub coat has essentially no influence on the active ingredient release characteristics. The subcoat is preferably essentially water-soluble, for instance it may consist of substances like hydroxypropylmethyl-cellulose (HPMC) as a film former. The average thickness of the subcoat layer is very thin, for example not more than 15 µm, preferably not more than 10 µm.

A top coat is also preferably essentially water soluble. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics.

The expressions sub coat and top coat are well known to the person skilled in the art.

Pharmaceutical or Nutraceutical Active Ingredients

The coating composition may comprise any or one or more pharmaceutical and/or nutraceutical active ingredients.

Nutraceutical Active Ingredients

The invention is preferably useful for nutraceutical dosage forms.

Nutraceuticals can be defined as extracts of foods claimed to have medical effects on human health. The nutraceutical is usual contained in a medical format such as capsule, tablet or powder in a prescribed dose. Examples for nutraceutical active ingredients are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flvonoids, antioxidants, alpha-linoleic acid from flax seed, beta-carotene from marigold petals or antocyanins from berries. Sometimes the expression neutraceuticals is used as synonym for nutraceuticals.

The gastric resistant pharmaceutical or nutraceutical composition is comprising a core, comprising a pharmaceutical or nutraceutical active ingredient. The pharmaceutical or nutraceutical active ingredient may be a pharmaceutical or nutraceutical active ingredient which may be inactivated under the influence of gastric fluids at pH 1.2 or a pharmaceutical or nutraceutical active ingredient which may irritate the stomach mucosa when set free in the stomach.

Pharmaceutical Active Ingredients

The invention is also preferably useful for enteric coated pharmaceutical dosage forms.

Preferred drug classes are those (including but not limited to) coming from parenteral to oral switch considerations and/or high potency drugs (e.g. cytostatics, hormons, hormon receptor agonists, hormon receptor antagonists) and/or drugs with high side effects and toxicity issues (including prodrug metabolization; e.g. peptides, peptidomimetics, nucleotides, nucleosides, nucloeside analogues, taxoids)

Especially preferred are the following drugs

Remicade® (Infliximab, Johnson & Johnson, Schering-Plough, Mitsubishi Tanabe Pharma—Crohn's disease, Rheumatoid arthritis), Enbrel® (Etanercept, Wyeth—Rheumatoid arthritis), Zyprexa® (Olanzapine, Eli Lilly and Company—Psychosis), Seroquel® (Quetiapine, AstraZeneca—Schizophrenia), Herceptin® (Trastuzumab, Roche, Genentech, Chugai Pharmaceutical—Breast cancer), Lexapro®, Cipralex® (Escitalopram, Forest Laboratories, H. Lundbeck—Depression, Anxiety disorders), Gleevec®, Glivec (Imatinib, Novartis—Leukemia), Avastin® (Bevacizumab, Roche, Genentech—Colorectal cancer), Taxotere® (Docetaxel, Sanofi-Aventis—Cancer), Eloxatin®, Eloxatine® (Oxaliplatin, Sanofi-Aventis—Colorectal cancer), Wellbutrin® (Bupropion, GlaxoSmithKline, Biovail—Depression, Seasonal affective disorder (SAD)), Abilify® (Aripiprazole, Otsuka Pharmaceutical, Bristol-Myers Squibb—Psychosis, Depression), Avonex® (Interferonbeta-1a, Biogen Idec—Multiple sclerosis), Viagra® (Sildenafil, Pfizer—Erectile dysfunction), Lupron®, Leuplin (Leuprolide, Takeda Pharmaceutical, TAP Pharmaceuticals—Prostate cancer), Zofran® (Ondansetron, GlaxoSmithKline—Nausea and vomiting), Arimidex® (Anastrozole, AstraZeneca—Breast cancer), Prograf® (Tacrolimus, Astellas Pharma—Transplant rejection), CellCept® (Mycophenolatemofetil, Roche, Chugai Pharmaceutical—Transplant rejection), Gemzar® (Gemcitabine, Eli Lilly and Company—Cancer), Cymbalta® (Duloxetine, Eli Lilly and Company—Depression, Anxiety disorders), Duragesic® (Fentanyl, Johnson & Johnson—Pain), Casodex® (Bicalutamide, AstraZeneca—Prostate cancer), Truvada® (Tenofovir+Emtricitabine, Gilead Sciences—HIV infection), Flomax® (Tamsulosin, Boehringer Ingelheim—Benign prostatic hypertrophy), Lyrica® (Pregabalin, Pfizer—Neuropathic pain), Paxil®, Seroxat® (Paroxetine, GlaxoSmithKline—Depression, Anxiety disorders), Kaletra® (Lopinavir, Abbott Laboratories—HIV infection), Erbitux® (Cetuximab, Bristol-Myers Squibb, Merck KGaA—Colorectal cancer), Zoladex® (Goserelin, AstraZeneca—Prostate cancer), Combivir® (Lamivudine+Zidovudine, GlaxoSmithKline—HIV infection), Cialis® (Tadalafil, Eli Lilly and Company, Lilly Icos—Erectile dysfunction), Reyataz® (Atazanavir, Bristol-Myers Squibb—HIV infection), Concerta® (Methylphenidate, Johnson & Johnson—Attention-deficit hyperactivity disorder), Camptosar® (Irinotecan, Pfizer—Colorectal cancer), Adderall® (Amphetamine, Shire Pharmaceuticals—Attention-deficit hyperactivity disorder), Ultane®, Sevorane® (Sevoflurane, Abbott Laboratories—Anesthesia), Xeloda® (Capecitabine, Roche, Chugai Pharmaceutical—Cancer), Femara® (Letrozole, Novartis, Chugai Pharmaceutical—Breast cancer), Viread® (Tenofovir, Gilead Sciences—HIV infection), Tarceva® (Erlotinib, Roche, Genentech—Non-small cell lung cancer), Alimta® (Pemetrexed, Eli Lilly and Company—Non-small cell lung cancer), Actiq® (Fentanyl, Cephalon—Cancer pain), Lidoderm® (Lidocaine, Endo Pharmaceuticals—Pain), Taxol® (Paclitaxel, Bristol-Myers Squibb—Cancer), Trizivir® (Abacavir+Lamivudine+Zidovudine, GlaxoSmithKline—HIV infection), Epzicom®, Kixeva® (Abacavir+Lamivudine, GlaxoSmithKline—HIV infection), Venlafaxine® (Effexor, Wyeth—Antidepressant)

. . . as well as drugs of the respective compound class thereof and/or the respective mode of action implied by said examples (as the latter is a descriptor of not only the physico-chemistry of the active pharmaceutical ingredient (API) but also its physiological behaviour and pharmaceutical character).

Therapeutical and chemical classes of drugs used in enteric coated pharmaceutical dosage forms are for instance analgetics, antibiotics or anti-infectives, antibodies, antiepileptics, antigens from plants, antirheumatics, betablocker, benzimidazole derivatives, beta-blocker, cardiovascular drugs, chemotherapeuitcs, CNS drugs, digitalis glycosides, gastrointestinal drugs, e.g. proton pum inhibitors, enzymes, hormons, liquid or solid natural extracts, oligonucleotides, peptidhormon proteins, therapeutical bacteria, peptides, proteins, proton pump inhibitors, (metal) salt f.e. aspartates, chlorides, orthates, urology drugs, vaccines Examples of drugs, which are acid-lablile, irritating or need controlled release, may be: Acamprosat, aescin, amylase, acetylsalicylic acid, adrenalin, 5-amino salicylic acid, aureomycin, bacitracin, balsalazine, beta carotene, bicalutamid bisacodyl, bromelain, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, omeprazole, orothates, pancreatin, pantoprazole, parathyroid hormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, thrypsine, valproic acid, vasopressin, vitamins, zinc, including their salts, derivatives, polymorphs, isomorphs, or any kinds of mixtures or combinations thereof.

Pharmaceutical or Nutraceutical Excipients (Coating Composition)

The coating composition may comprise may comprise, essentially comprise or contain up to 80, up to 70, up to 60, up to 50, up to 40, up to 30, up to 20% by weight or any pharmaceutical or nutraceutical excipients. Thus the amounts of the enteric core/shell polymer and the pharmaceutical or nutraceutical excipients may add up to 100% in the coating composition.

In some cases it may be useful that the coating composition may also comprise, additionally to the active ingredient in the core, a partial amount, preferably less than 10% less than 5% less than 2% by weight of the total amount of one or more pharmaceutical or nutraceutical active ingredients, for instance in order to provide a fast released initial dose. In this case the coating composition has the function as a binding agent or as a binder for the additional portion of active ingredient. Thus in this case the amounts the enteric core/shell polymer, the pharmaceutical or nutraceutical excipients and the one or more pharmaceutical or nutraceutical active ingredients may add up to 100% in the coating composition.

The coating composition may comprise up to 80, up to 70, up to 60, up to 50, up to 40, up to 30, up to 20% by weight or any of pharmaceutical or nutraceutical excipients selected from the group of antioxidants, brighteners, binding agents, flavouring agents, flow aids, fragrances, glidants, penetration-promoting agents, pigments, plasticizers, polymers, which are different from the core/shell polymers described herein, pore-forming agents or stabilizers.

Gastric Resistant Pharmaceutical or Nutraceutical Dosage Form

The invention relates to a gastric resistant pharmaceutical or nutraceutical dosage form, comprising a core, comprising a pharmaceutical or nutraceutical active ingredient and a gastric resistant coating layer onto the core, wherein the gastric resistant coating layer is derived from the coating composition as described herein.

The gastric resistant pharmaceutical or nutraceutical dosage form according to the invention is characterized by the release of the pharmaceutical or nutraceutical active ingredient according to USP, which is not more than 10, not more than 8 or not more than 5% under in-vitro conditions at pH 1.2 after 2 hours in 1 molar HCl with and without the addition of 20% (v/v) ethanol.

The gastric resistant pharmaceutical or nutraceutical composition according to the invention may be further characterized by the release of the pharmaceutical or nutraceutical active ingredient according to USP, which is at least 50, at least 60, at least 80% under in-vitro conditions at pH 6.8 after 45 minutes in a buffered medium (phosphate buffered saline, pH 6.8, European Pharmacopoeia 4003200).

Reference is made to USP32/NF27 (NF=National Formulary), apparatus II, paddle method, 50 rpm for tablets or paddle or basket method 50 to 100 rpm, depending on the monography, for pellets.

Use as a Coating Composition

The invention relates to the use of a coating composition as described herein for the coating of a core, comprising a pharmaceutical or nutraceutical active ingredient, wherein the resulting coated pharmaceutical or nutraceutical dosage form shows a release of the pharmaceutical or nutraceutical active ingredient of not more than 10% under in-vitro conditions at pH 1.2 after 2 hours in medium according to USP with and without the addition of 20% (v/v) ethanol.

Use as a Binding Composition

The coating composition as described in here may as well be used as a binding agent for the binding of a pharmaceutical or nutraceutical active ingredient in a coating or in the core of a pharmaceutical or nutraceutical dosage form. When the coating composition is not used in a coating but used as a binding agent in the core of a pharmaceutical or nutraceutical dosage form, as a binder or as a matrix former, it may be rather called a binding composition.

Release of the Pharmaceutical or Nutraceutical Active Ingredient for the Binding Composition The release of the pharmaceutical or nutraceutical active ingredient is not more than 10, not more than 8 or not more than 5% under in-vitro conditions at pH 1.2 after 2 hours in medium according to USP with and without the addition of 20, 30 or 40% (v/v) ethanol.

The release of the pharmaceutical or nutraceutical active ingredient is at least 50, at least 60, at least 80% under in-vitro conditions at pH 6.8 after 45 or after 60 minutes in buffered medium according to USP.

The USP (USP=United States Pharmacopoeia) which may be preferably used is USP32/NF27 (NF=National Formulary), apparatus II, paddle method, 50 rpm for tablets or paddle or basket method 50 to 100 rpm, depending on the monograph, for pellets.

Core/Shell Polymer Composition

The invention also relates to a core/shell polymer composition as described herein for use as a coating or binding agent in a pharmaceutical or nutraceutical dosage form.

The core/shell polymer composition is derived from an emulsion polymerisation process, wherein either the core is formed by a water-insoluble polymer or copolymer and the shell is formed an anionic polymer or copolymer or vice versa.

A core/shell polymer composition is wherein the core is formed by a water-insoluble polymer or copolymer and the shell is formed an anionic polymer or copolymer is preferred.

The invention therefore relates to a core/shell polymer composition, suitable as coating or binding agent for a pharmaceutical or nutraceutical dosage form, comprising a core and an outer coating, where the core is comprising one or more pharmaceutical or nutraceutical active ingredients and where the coating is comprising the core/shell polymer composition, which is derived from an emulsion polymerisation process, wherein either the core of the core/shell polymer composition is formed by a water-insoluble, not cross-linked polymer or copolymer and the shell is formed an anionic polymer or copolymer or vice versa. Thus the core/shell polymer composition is a part of the pharmaceutical or nutraceutical dosage form.

Although the monomers for the water-insoluble, not cross-linked polymer or copolymer are preferably fed first in the emulsion polymerization step to form the core of the core/shell composition and the monomers for the anionic polymer or copolymer are fed thereafter to form the shell, an inversion may take place where core and shell exchange their position during the process.

Likewise as described in WO2008/049657 the inventive core/shell polymer compositions may be useful as binding agents or matrix formers for active ingredients included in retarded or sustained release oral dosage forms in order to minimize the effect of acceleration or deceleration of the active ingredient release by the influence of ethanol under in-vitro conditions.

EXAMPLES

Preparation of a Polymer Dispersion, According to the Invention

The polymer was prepared in a 1 liter round bottom flask, equipped with a lid, an anchor stirrer, a baffle, a reflux condenser, a feed pipe for nitrogen and a temperature probe to monitor the temperature inside the reactor. A water bath with a thermostat was used to control the reaction temperature.

653 g of deionized water, 13.2 g of sodium dodecylsulfate solution (15% in water; Disponil SDS 15) and 6.5 g of polysorbate 80 (TEGO SMO 80V) were charged into the flask. The reactor was flushed with nitrogen and the mixture was agitated with the stirrer and heated to a starting temperature of 82° C.

Two stable monomer emulsions were prepared for the core polymer and the shell polymer respectively. In sum 280.0 g of monomers were used, divided between the two flasks according to the desired ratio of core polymer to shell polymer. The monomer composition of each of the two emulsions was chosen according to the table of examples (see below). For each emulsion 3% by weight of deionized water, based on the weight of monomers, was used.

As an example for "Core Shell polymer composition A"—as in the table of examples—the core monomer emulsion was prepared with 70.0 g of methacrylic acid, 70.0 g of ethyl acrylate and 4.2 g of deionized water. The shell monomer emulsion was prepared from 98.0 g of methyl methacrylate, 42.0 g of ethyl acrylate and 4.2 g of deionized water.

Two initiator solutions (for the preparation of the core polymer and the shell polymer, respectively) were prepared, by dissolving 0.12 mol % ammonium persulfate (with regard to the sum of used monomers of the core monomer emulsion and the shell monomer emulsion, respectively) in 5.0 g of deionized water.

When the temperature inside the reactor had reached 82° C., the initiator solution for the core polymer is added to the reactor. Two minutes later, the dosing of the core monomer emulsion was started at a dosing rate of 2 g/min. By adjusting the temperature of the water bath, the temperature inside the reactor was kept at 82° C. After all the core monomer emulsion was added, the temperature was kept for 10 minutes at 82° C., before the initiator solution for the shell was added to the reactor. 2 minutes later, the dosing of the shell monomer emulsion was started at a dosing rate of 2 g/min.

After all the shell monomer emulsion was added, the temperature was kept for another 30 minutes at 82° C., before the reactor content was allowed to cool down to 20° C. and was filtered through a 250 μm gaze.

Preparation of a Spraying Suspension 8.8 g of triethyl citrate, 210.0 g of micronized talc and 1057 g deionized water were charged into a vessel and homogenized for 15 minutes with an ULTRA TURRAX high-performance dispersing instrument.

350.0 g of the polymer dispersion (30% solids content) is stirred with a magnetic stirrer. After the talcum dispersion is slowly poured into to polymer dispersion, the stirring is continued for 60 minutes, before the mixture is filtered through a 240 μm gaze.

Coating Process

A MicroLab coater (Oystar Hüttlin) was used to prepare the coatings.

350 g of metoprolol succinate pellets (diameter 0.7-1.0 mm, 20% active content) were charged into the MicroLab instrument and agitated with low air supply. In one example 350 g of diprophylline pellets (diameter 0.8-1.0 mm, 50% active content) were used instead. The fluid bed temperature was raised to 23-26° C. and the pellets were coated for 1.5 to 2.5 hour up to a polymer weight gain of 10.5 or 17.5% (additional weight due to polymer in coating with respect to initial pellet weight). The spray rate was raised slowly to a maximum of 2 g/min.

After the coating process, the pellets were agitated in the instrument for another 5 minutes for additional drying and curing. Then the coated pellets were allowed to cool down in the instrument with low air supply.

TABLE 2

Core Shell polymer compositions A-D

| Trial | Core/Shell weight ratio | Core copolymer Monomer composition [% by weight] | Shell copolymer Monomer composition [% by weight] |
|---|---|---|---|
| Core Shell polymer composition A | 50/50 | 50 MAA<br>50 EA | 70 MMA<br>30 EA |
| Core Shell polymer composition B | 50/50 | 70 MMA<br>30 EA | 50 MAA<br>50 EA |
| Core Shell polymer composition C | 80/20 | 70 MMA<br>30 EA | 50 MAA<br>50 EA |
| Core Shell polymer composition D | 50/50 | 70 MMA<br>30 EA | 10 MAA<br>65 MA<br>25 MMA |

MAA = methacrylic acid
EA = ethyl acrylate
MMA = methyl methacrylate
MA = methyl acrylate

TABLE 3

| | poylmer weight gain [%] | Active Ingredient | Active Ingredient Release [%] | | |
|---|---|---|---|---|---|
| | | | after 120 min at pH 1.2 | after 120 min at pH 1.2 + 45 min at pH 6.8 | after 120 min at pH 1.2 with addition of 20% ethanol |
| Core Shell polymer composition A | 17.5 | Metoprolol Succinate | 0.4 | 92.9 | 0.3 |
| Core Shell polymer composition B | 17.5 | Metoprolol Succinate | 0.0 | 88.7 | 2.4 |
| Core Shell polymer composition B | 17.5 | Diprophylline | 0.0 | 100.0 | 4.7 |
| Core Shell polymer composition C | 17.5 | Metoprolol Succinate | 0.0 | 89.6 | 0.0 |
| Core Shell polymer composition D | 10.5 | Metoprolol Succinate | 1.6 | 71.8 | 2.5 |

Analytical Methods
Partcle Size rMS [nm]

The particle size was determined by laser diffraction, using a Mastersizer 2000 (Malvern). The values are indicated as particle radius rMS [nm], which is half of the median of the volume based particle size distribution d(v, 50).

Viscosity Number Vz [mL/g]

The viscosity number Vz is often used as a measure for the molecular weight. It was determined in accordance with DIN EN ISO 1628-1.

A process controlled viscosity measuring system (PVS, Lauda GmbH & Co. KG) with an Ubbelohde capillary (type Oc) was used.

The polymer was dissolved in THF, at a concentration of 0.5 g per 100 mL of solvent. The temperature of the measurement was 25° C.

Molecular Weight Mw [g/mol]

The molecular weight was determined by gel permeation chromatography (GPC). The molar mass calibration was based on poly(methyl methacrylate).

The conditions of the measurement were chosen according to the publication of Martina Adler et. al. (e-Polymers 2004, 055).

N,N-Dimethylacetamide with 6 g/L acetic acid, 3 g/L LiBr and 10 g/L $H_2O$ was used as a mobile phase, with a flow rate of 1.0 ml/min. A column set of 4 GRAM 10 μm columns (precolumn, 2×10.000 Å and 30 Å column—Polymer Standards Service, Mainz, Germany) was used as stationary phase.

Glass Transition Temperature Tg [° C.]

The glass transition temperature Tg was determined by DSC according to DIN EN ISO 11357. Typically between 10 and 12 mg sample, and a heating rate of 20 K/min was used; the temperature range was −40° C. to 140° C. The measurement is carried out under nitrogen atmosphere. The evaluation was based on the second heating cycle, and the indicated value is the mean value in the glass transition interval.

Minimum Film-Forming Temperature MFT [° C.]

The lowest temperature at which a polymer-dispersion will form a polymer film upon evaporation of the water is the minimum film-forming temperature (MFT). The MFT is characteristic of the dispersion and is—amongst others—influenced by the glass transition temperature and the particle size of the dispersed particles.

The minimum film-forming temperature has been determined according to DIN ISO 2115 by applying the dispersion with a doctor knife on a band heater at a defined temperature gradient. The MFT corresponds to the lowest temperature at which a crack-free film is formed and is slightly above the whitening point (which is the temperature at which the polymer still appears whitish because the film has not yet fully been formed).

Active Ingredient Release

The release properties were determined in a dissolution apparatus (USP 32 <711> dissolution; type 1: basket), at a rotation speed of 100 rpm, with 900 mL of dissolution medium. The temperature was 37° C.±0.5° C.

The dissolution medium was 0.1 N hydrochloric acid (0.1 N HCl) for 2 hours; then a full exchange of the dissolution medium to pH 6.8 EP-buffer 4003200 (=phosphate buffered saline: 8.5 g NaCl, 1 g $KH_2PO_4$, 2 $K_2HPO_4$ in 1 L $H_2O$) was done. The amount of released API (diprophylline or metoprolol succinate, respectively) was determined by UV-measurements.

The effect of ethanol was studied by replacing a part of the hydrochloric acid with ethanol. Measurements with 20% ethanol (by volume) were carried out.

The dissolution medium after the full exchange to pH 6.8 did not contain any ethanol (in all cases).

The invention claimed is:

1. A coating composition consisting essentially of components suitable for the coating a pharmaceutical or nutraceutical dosage form, comprising:
   at least 20% by weight of an enteric core/shell polymer composition derived from an emulsion polymerization process whereby (1) core polymer particles are formed by monomer polymerization in an emulsion, and (2) the shell is polymerized onto the core polymer particles by subsequent monomer polymerization in the same emulsion,
   wherein the enteric core/shell polymer composition has an homogeneous microstructure without visible phase separation; and
   wherein either the core polymer of the core/shell polymer composition is a water-insoluble, not cross-linked polymer or copolymer and the shell polymer of the core/shell polymer composition is an anionic polymer or copolymer, or the shell polymer of the core/shell polymer composition is a water-insoluble, not cross-linked polymer or copolymer and the core polymer of the core/shell polymer composition is an anionic polymer or copolymer.

2. The coating composition according to claim 1, further comprising up to 80% by weight of at least one pharmaceutical or nutraceutical excipient selected from the group consisting of an antioxidant, a brightener, a binding agent, a flavouring agent, a flow aid, a fragrance, a glidant, a penetration-promoting agent, a pigment, a plasticizer, a polymer, a pore-forming agent and a stabilizer.

3. The coating composition according to claim 1, wherein the composition is present in the form of a solid phase of an aqueous dispersion with a solid content of from 1 to 60% by weight.

4. The coating composition according to claim 1, wherein the composition is present in the form of a dry powder or a granulate.

5. The coating composition according to claim 1, wherein the water-insoluble polymer or copolymer is selected from the group consisting of (meth)acrylate polymer, (meth)acrylate copolymer, polyvinyl polymer, polyvinyl copolymer, and cellulose having not more than 12% by weight of monomer residues with an ionic functional group.

6. The coating composition according to claim 1, wherein the anionic polymer or copolymer is selected from the group consisting of (meth)acrylate polymer, (meth)acrylate copolymer having from 5 to 75% by weight of monomeric residues with an anionic functional group, polyvinyl polymer, polyvinyl copolymer, and cellulose.

7. The coating composition according to claim 1, wherein the coating composition comprises a pharmaceutical or nutraceutical active ingredient, and the composition is suitable for coating a pharmaceutical or nutraceutical dosage form.

8. A gastric resistant pharmaceutical or nutraceutical dosage form, comprising:
a core comprising a pharmaceutical or nutraceutical active ingredient; and
a gastric resistant coating layer coating the core,
wherein the gastric resistant coating layer is the coating composition according to claim 1,
wherein a release of the pharmaceutical or nutraceutical active ingredient is not more than 10% under in-vitro conditions at pH 1.2 after 2 hours in medium according to USP with and without the addition of 20% (v/v) ethanol, and
wherein a release of the pharmaceutical or nutraceutical active ingredient is at least 50% under in-vitro conditions at pH 6.8 or pH 7.2 after 45 minutes in a buffered medium according to USP.

9. The dosage form according to claim 8, wherein a release of the pharmaceutical or nutraceutical active ingredient is not more than 5% under in-vitro conditions at pH 1.2 after 2 hours in medium according to USP with and without the addition of 20% (v/v) ethanol.

10. The dosage form according to claim 8, wherein a release of the pharmaceutical or nutraceutical active ingredient is at least 80% under in-vitro conditions at pH 6.8 or pH 7.2 after 45 minutes in a buffered medium according to USP.

11. The coating composition according to claim 1, applied to a core comprising a pharmaceutical or nutraceutical active ingredient to form a pharmaceutical or nutraceutical dosage form, wherein a resulting pharmaceutical or nutraceutical dosage form shows a release of the pharmaceutical or nutraceutical active ingredient of not more than 10% under in-vitro conditions at pH 1.2 after 2 hours in medium according to USP with and without the addition of 20% (v/v) ethanol.

12. The coating composition according to claim 1, wherein the composition is suitable as a binding agent for binding of a pharmaceutical or nutraceutical active ingredient in a coating or as a matrix former in the core of a pharmaceutical or nutraceutical dosage form.

13. A core/shell polymer composition consisting essentially of components suitable for the coating a pharmaceutical or nutraceutical dosage form,
wherein the core/shell polymer composition is derived from an emulsion polymerization process whereby (1) core polymer particles are formed by monomer polymerization in an emulsion, and (2) the shell is polymerized onto the core polymer particles by subsequent monomer polymerization in the same emulsion;
wherein the core/shell polymer composition has an homogeneous microstructure without visible phase separation; and
wherein either the core polymer of the core/shell polymer composition is a water-insoluble, not cross-linked polymer or copolymer and the shell polymer of the core/shell polymer composition is an anionic polymer or copolymer, or the shell polymer of the core/shell polymer composition is a water-insoluble, not cross-linked polymer or copolymer and the core polymer of the core/shell polymer composition is an anionic polymer or copolymer.

14. The core/shell polymer composition according to claim 13, wherein a weight of the core polymer is from 10 to 95% of a weight of the total composition.

15. The core/shell polymer composition according to claim 13, wherein the core polymer of the core/shell polymer composition is formed by a water-insoluble, not cross-linked polymer or copolymer and the shell polymer of the core/shell polymer composition is formed by an anionic polymer or copolymer.

16. The core/shell polymer composition according to claim 13, wherein the shell polymer of the core/shell polymer composition is formed by a water-insoluble, not cross-linked polymer or copolymer and the core polymer of the core/shell polymer composition is formed by an anionic polymer or copolymer.

17. The core/shell polymer composition according to claim 13, wherein the core/shell polymer composition is obtained by an emulsion polymerization process in the same emulsion.

18. The coating composition according to claim 1, wherein the core polymer of the core/shell polymer composition is a water-insoluble, not cross-linked polymer or copolymer and the shell polymer of the core/shell polymer composition is an anionic polymer or copolymer.

19. The coating composition according to claim 1, wherein the water-insoluble polymer or copolymer is selected from the group consisting of (meth)acrylate polymer, (meth)acrylate copolymer, polyvinyl polymer, polyvinyl copolymer, and cellulose having not more than 12% by weight of monomer residues with an ionic functional group and the anionic polymer or copolymer is selected from the group consisting of (meth)acrylate polymer, (meth)acrylate copolymer having 5-75% by weight of monomer residues with an anionic functional group, polyvinyl polymer, polyvinyl copolymer, and cellulose.

20. The core/shell polymer composition according to claim 13, wherein the water-insoluble polymer or copolymer is selected from the group consisting of (meth)acrylate polymer, (meth)acrylate copolymer, polyvinyl polymer, polyvinyl copolymer, and cellulose having not more than 12% by weight of monomer residues with an ionic functional group and the anionic polymer or copolymer is selected from the group consisting of (meth)acrylate polymer, (meth)acrylate copolymer having 5-75% by weight of monomer residues with an anionic functional group, polyvinyl polymer, polyvinyl copolymer, and cellulose.

21. A gastric resistant pharmaceutical or nutraceutical dosage form, comprising:
    a core comprising a pharmaceutical or nutraceutical active ingredient; and
    a gastric resistant coating layer coating the core,
    wherein the gastric resistant coating layer is a coating composition comprising the core/shell polymer composition according to claim 13.

22. The core/shell polymer composition according to claim 13, wherein the core/shell polymer composition is obtained by a monomer emulsion feed polymerization process in the same emulsion.

23. The coating composition according to claim 1, wherein the anionic polymer or copolymer is an anionic (meth)acrylate copolymer comprising polymerized units of:
    10 to 40% by weight of acrylic or methacrylic acid,
    10 to 50% by weight of ethyl acrylate,
    10 to 80% by weight of a C4- to C18-alkyl ester of acrylic or methacrylic acid, and
    optionally 0 to 20 by weight of methyl methacrylate;
or polymerized units of:
    40 to 60% by weight methacrylic acid, and
    60 to 40% by weight methyl methacrylate or 60 to 40% by weight ethyl acrylate;
or polymerized units of:
    20 to 40% by weight methacrylic acid and
    80 to 60% by weight methyl methacrylate;
or polymerized units of:
    10 to 30% by weight methyl methacrylate,
    50 to 70% by weight methyl acrylate, and
    5 to 15% by weight methacrylic acid.

24. The core/shell polymer composition according to claim 13, wherein the anionic polymer or copolymer is an anionic (meth)acrylate copolymer comprising polymerized units of:
    10 to 40% by weight of acrylic or methacrylic acid,
    10 to 50% by weight of ethyl acrylate,
    10 to 80% by weight of a C4- to C18-alkyl ester of acrylic or methacrylic acid, and
    optionally 0 to 20 by weight of methyl methacrylate;
or polymerized units of:
    40 to 60% by weight methacrylic acid, and
    60 to 40% by weight methyl methacrylate or 60 to 40% by weight ethyl acrylate;
or polymerized units of:
    20 to 40% by weight methacrylic acid and
    80 to 60% by weight methyl methacrylate;
or polymerized units of:
    10 to 30% by weight methyl methacrylate,
    50 to 70% by weight methyl acrylate, and
    5 to 15% by weight methacrylic acid.

* * * * *